United States Patent
Margulis

(10) Patent No.: US 9,767,537 B1
(45) Date of Patent: Sep. 19, 2017

(54) SYSTEM AND METHOD FOR INSPECTION USING PROGRAMMABLE FILTERS

(71) Applicant: APPLIED MATERIALS ISRAEL LTD., Rehovot (IL)

(72) Inventor: Pavel Margulis, Ashdod (IL)

(73) Assignee: APPLIED MATERIALS ISRAEL LTD., Rehovot (IL)

(*) Notice: Subject to any disclaimer, the term of this patent is extended or adjusted under 35 U.S.C. 154(b) by 0 days.

(21) Appl. No.: 15/134,298

(22) Filed: Apr. 20, 2016

(51) Int. Cl.
| | |
|---|---|
| G06K 9/00 | (2006.01) |
| G06T 5/00 | (2006.01) |
| G06T 7/00 | (2017.01) |
| G06T 5/20 | (2006.01) |

(52) U.S. Cl.
CPC ............. G06T 5/002 (2013.01); G06T 5/20 (2013.01); G06T 7/001 (2013.01); G06T 7/0008 (2013.01); *G06T 2207/20024* (2013.01); *G06T 2207/20182* (2013.01); *G06T 2207/30141* (2013.01); *G06T 2207/30148* (2013.01)

(58) Field of Classification Search
None
See application file for complete search history.

(56) References Cited

U.S. PATENT DOCUMENTS

| | | | | |
|---|---|---|---|---|
| 6,201,601 B1* | 3/2001 | Vaez-Iravani | ............. | G01J 3/44 356/237.4 |
| 7,304,310 B1* | 12/2007 | Shortt | ............. | G01N 21/94 250/372 |
| 7,436,505 B2* | 10/2008 | Belyaev | ............. | G01N 21/9501 356/237.2 |
| 7,570,797 B1* | 8/2009 | Wang | ............. | G01N 21/9501 250/559.45 |
| 9,177,370 B2* | 11/2015 | Chen | ............. | G06T 7/0004 |

* cited by examiner

*Primary Examiner* — Feng Niu
(74) *Attorney, Agent, or Firm* — Kilpatrick Townsend & Stockton LLP

(57) ABSTRACT

An inspection system that includes a memory; a configurable acquisition channel; a controller that is adapted to: (a) determine, in response to a first frequency wise relationship between the first noise power spectrum and the first signal power spectrum, a first configuration of the configurable acquisition channel; and (b) determine, in response to a second frequency wise relationship between the second noise power spectrum and the second signal power spectrum, a second configuration of the configurable acquisition channel; and wherein the configurable acquisition channel is adapted to: (a) acquire the image of the first area of the inspected object while being configured according to the first area configuration, and (b) acquire the image of the second area while being configured according to the second area configuration.

15 Claims, 9 Drawing Sheets

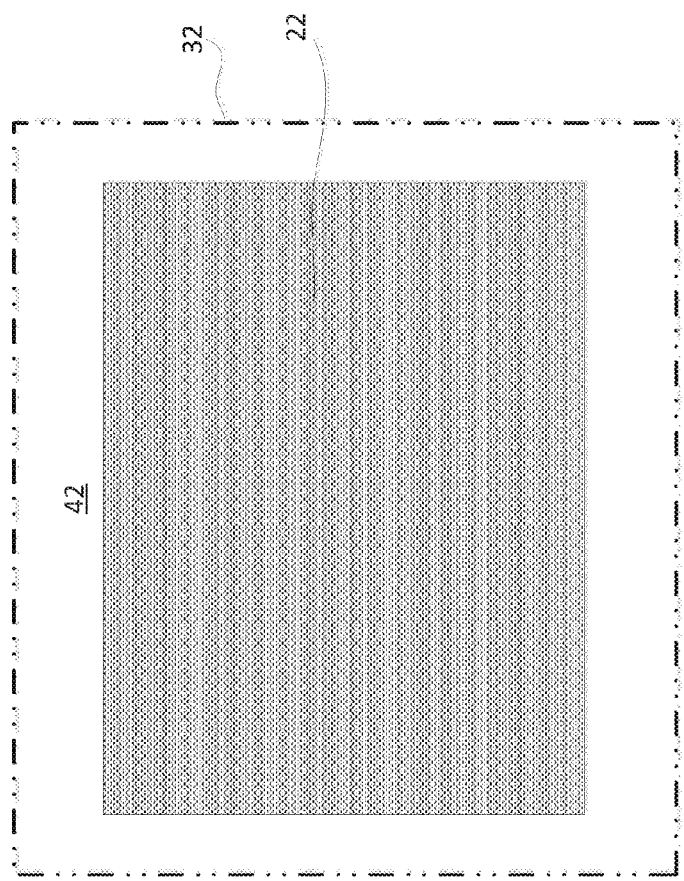
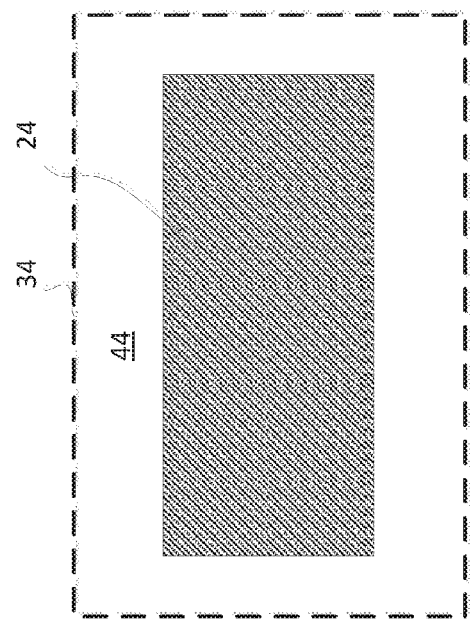
Fig. 5

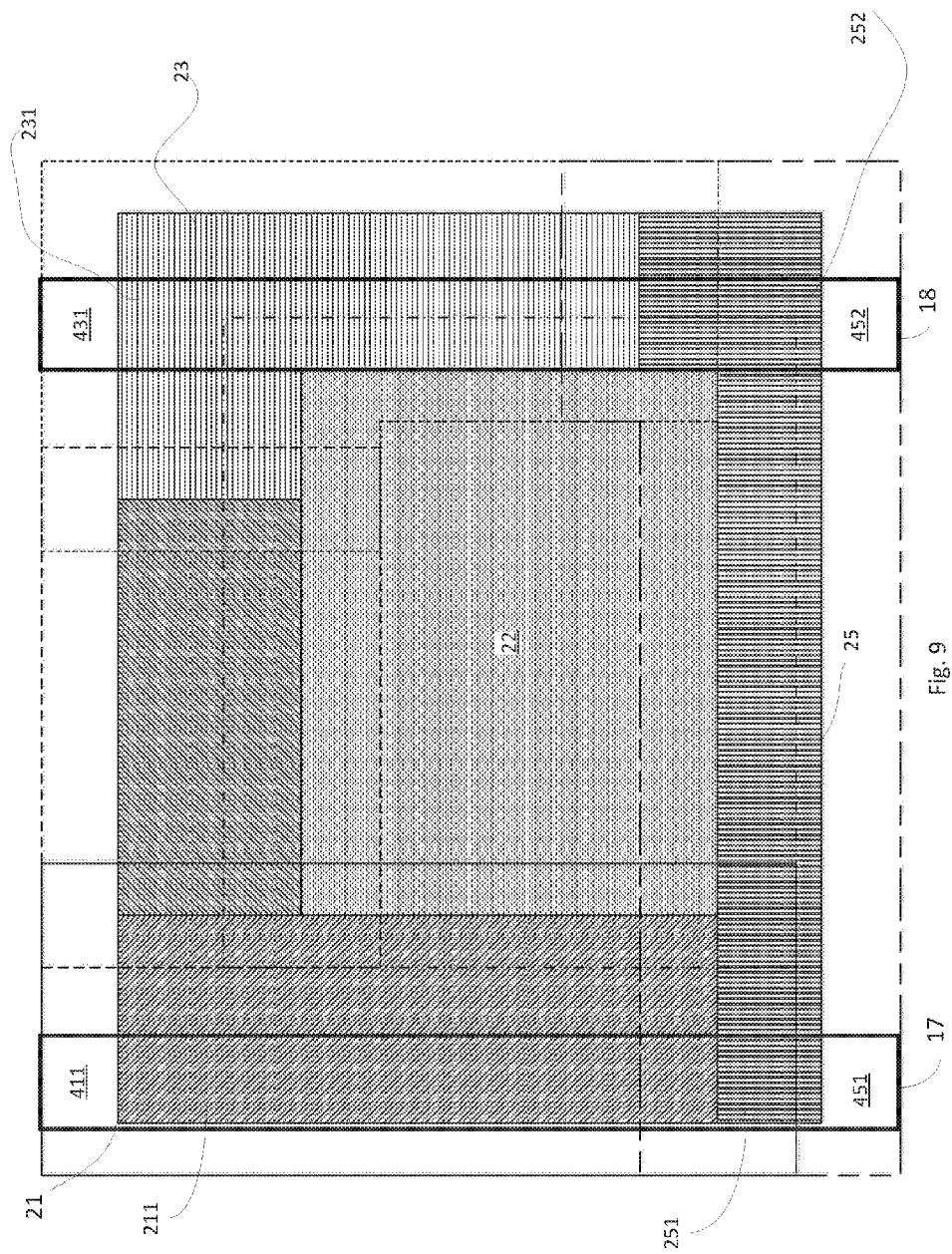

SYSTEM AND METHOD FOR INSPECTION USING PROGRAMMABLE FILTERS

BACKGROUND

Inspection systems acquire images of areas of an inspected object during an inspection process that is prone to noises and inconsistencies in the acquisition process.

These noises and inconsistencies may differ from area of the inspected object to another area—leading to reduction in the quality of the inspection process.

There is a growing need to improve the quality of the inspection process.

SUMMARY

According to an embodiment of the invention there may be provided an inspection system that may include (i) a memory module that may be adapted to store (a) first noise power spectrum information about noises associated with an acquisition of an image of a first area of an inspected object, (b) first signal power spectrum information about first area signals that may be associated with the acquisition of the image of the first area, (c) second noise power spectrum information about noises associated with an acquisition of an image of a second area of the inspected object, wherein the second area differs from the first area, and (d) second signal power spectrum information about second area signals that may be associated with the acquisition of the image of the second area; (ii) a configurable acquisition channel; (iii) a controller that may be adapted to (a) determine, in response to a first frequency wise relationship between the first noise power spectrum and the first signal power spectrum, a first configuration of the configurable acquisition channel; and (b) determine, in response to a second frequency wise relationship between the second noise power spectrum and the second signal power spectrum, a second configuration of the configurable acquisition channel. The configurable acquisition channel may be adapted to: (a) acquire the image of the first area of the inspected object while being configured according to the first area configuration, and (b) acquire the image of the second area while being configured according to the second area configuration.

The inspection system may include an image processor that may be adapted to: (a) process the image of the first area to generate a first area inspection result and (b) process the image of the second area to generate a second area inspection result.

The image processor may be adapted to: (a) generate an image of a first region by surrounding the image of the first area with first additional pixels; (b) process the image of the first region to provide a first area inspection result; (c) generate an image of a second region by surrounding the image of the second area with second additional pixels; and (d) process the image of the second region to provide a second area inspection result.

The first frequency wise relationship may be a frequency wise ratio between the first signal power spectrum and the first noise power spectrum; and wherein the second frequency wise relationship may be a frequency wise ratio between the second signal power spectrum and the second noise power spectrum.

The first frequency wise relationship may be a frequency wise ratio between the first signal power spectrum and a square of the first noise power spectrum; and wherein the second frequency wise relationship may be a frequency wise ratio between the second signal power spectrum and a square of the second noise power spectrum.

The first area and the second area may be selected so that the first frequency wise relationship differs from the second frequency wise relationship.

According to an embodiment of the invention there may be provided a method for inspecting an inspected object, the method may include (i) storing, at a memory module, (a) first noise power spectrum information about noises associated with an acquisition of an image of a first area of an inspected object, (b) first signal power spectrum information about first area signals that may be associated with the acquisition of the image of the first area, (c) second noise power spectrum information about noises associated with an acquisition of an image of a second area of the inspected object, wherein the second area differs from the first area, and (d) second signal power spectrum information about second area signals that may be associated with the acquisition of the image of the second area; (ii) determining, by a controller and in response to a first frequency wise relationship between the first noise power spectrum and the first signal power spectrum, a first configuration of a configurable acquisition channel; (iii) determining, by the controller and in response to a second frequency wise relationship between the second noise power spectrum and the second signal power spectrum, a second configuration of the configurable acquisition channel; (iv) acquiring, by the configurable acquisition channel, the image of the first area of the inspected object while the configurable acquisition channel may be configured according to the first area configuration; and (v) acquiring, by the configurable acquisition channel, the image of the second area of the inspected object while the configurable acquisition channel may be configured according to the second area configuration.

The method may include processing, by an image processor, the image of the first area to generate a first area inspection result; and processing, by the image processor, the image of the second area to generate a second area inspection result.

According to an embodiment of the invention there may be provided a non-transitory computer readable medium that stores instructions that once executed by a computer cause the computer to store: (a) first noise power spectrum information about noises associated with an acquisition of an image of a first area of an inspected object, (b) first signal power spectrum information about first area signals that may be associated with the acquisition of the image of the first area, (c) second noise power spectrum information about noises associated with an acquisition of an image of a second area of the inspected object, wherein the second area differs from the first area, and (d) second signal power spectrum information about second area signals that may be associated with the acquisition of the image of the second area; determine, in response to a first frequency wise relationship between the first noise power spectrum and the first signal power spectrum, a first configuration of a configurable acquisition channel; determine, in response to a second frequency wise relationship between the second noise power spectrum and the second signal power spectrum, a second configuration of the configurable acquisition channel; acquire the image of the first area of the inspected object while the configurable acquisition channel may be configured according to the first area configuration; and acquire the image of the second area of the inspected object while the configurable acquisition channel may be configured according to the second area configuration.

The non-transitory computer readable medium may store instructions for processing, by an image processor, the image of the first area to generate a first area inspection result; and processing, by the image processor, the image of the second area to generate a second area inspection result.

BRIEF DESCRIPTION OF THE DRAWINGS

The subject matter regarded as the invention is particularly pointed out and distinctly claimed in the concluding portion of the specification. The invention, however, both as to organization and method of step, together with objects, features, and advantages thereof, may best be understood by reference to the following detailed description when read with the accompanying drawings in which:

FIGS. 4, 5 and 6 illustrate first to fifth areas, additional pixels and first to fifth regions according to an embodiment of the invention;

FIG. 9 illustrates slices and multiple regions according to an embodiment of the invention.

Figure 1:
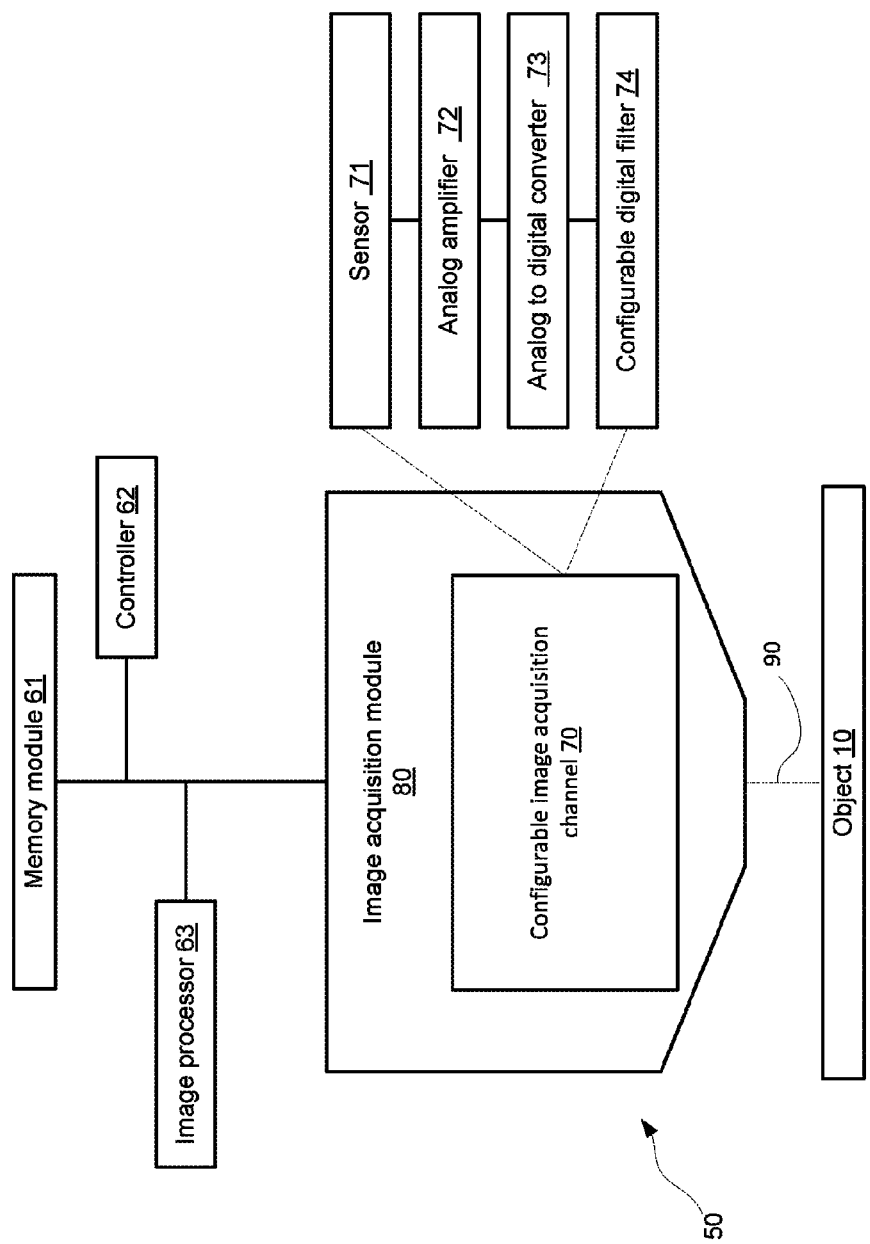
FIG. 1 illustrates a system and an object according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may, for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The term signal to noise ratio (SNR) means a ratio between a signal and a noise. The signal is a noise free signal that includes data about an inspected area of an object. In ideal conditions an inspection system will acquire only signals. In reality the inspection system acquires a combination of signals and noises.

Figure 2:
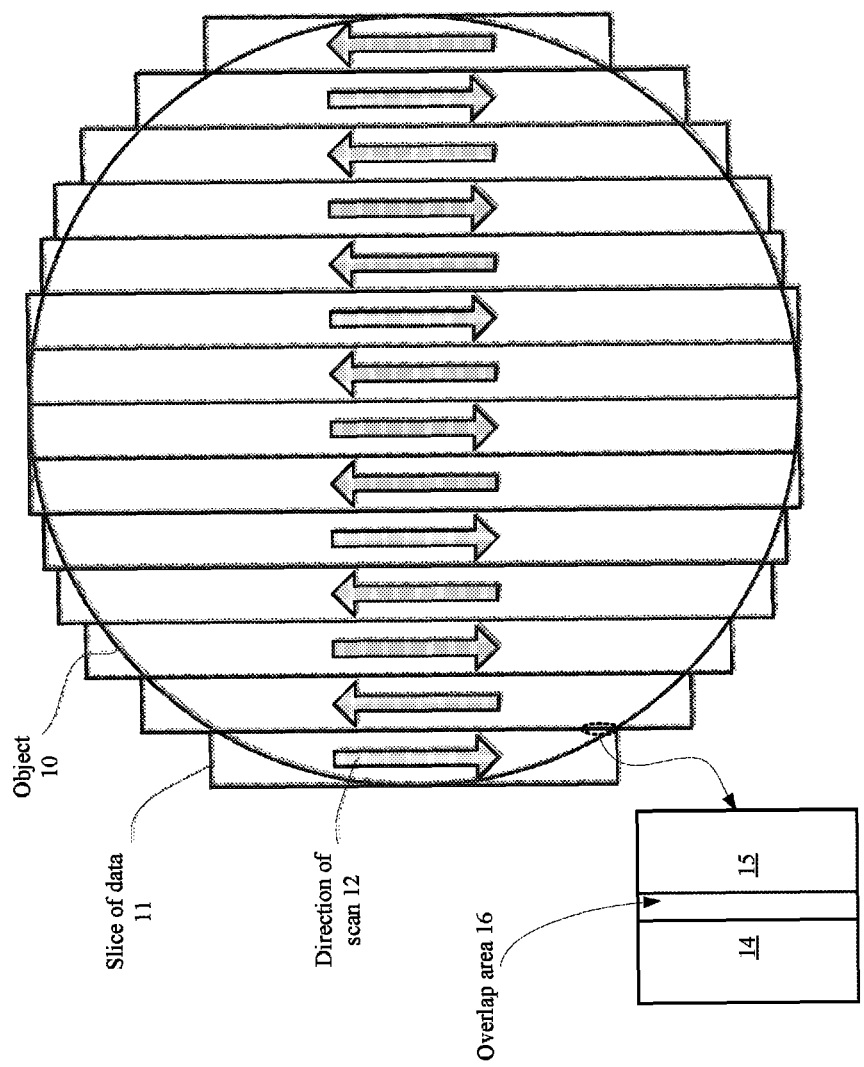
FIG. 2 illustrates a raster scan pattern according to an embodiment of the invention.

An inspection system may scan an inspected object, during an inspection process, by using a configurable image acquisition channel. FIG. 2 illustrates the mechanical scan pattern that virtually scans the object 10 one slice 11 after the other at alternating scan directions 12. FIG. 2 also shows that adjacent slices may include overlapping areas—such as overlap area 16 defined between a portion 14 of slice 11 and a portion 15 of an adjacent slice.

It has been found that improved inspection process capabilities can be obtained in relation to an image of an area of the inspected object when a frequency response of the configurable image acquisition channel is selected based on a frequency wise relationship between (a) a power spectrum of a noise associated with the acquisition of the image of the area of the inspected object, and (b) a power spectrum of a signal associated with the acquisition of the image of the area of the inspected object.

FIG. 1 illustrates inspection system 50 and an object 10 according to an embodiment of the invention.

Inspection system 50 includes memory module 61, controller 62, image processor 63 and image acquisition module 80.

The image acquisition module 80 may include one or more configurable image acquisition channels such as configurable image acquisition channel 70.

FIG. 1 illustrates the configurable image acquisition channel 70 as including (a) analog components such as sensor 71 for generating detection signals, analog amplifier 72 for amplifying the detection signals to provide analog amplified signals, (b) an analog to digital converter 73 that is adapted to convert the analog amplified signals to digital signals and a (c) digital components such as configurable digital filter 74 that is arranged to apply a filtering operation on the digital signals to provide filtered signals that may be further processed by image processor 63. The configurable digital filter 74 may be implemented by a software executed by image processor 63.

It is noted that usually digital components are easier to configure and control than analog components.

Object 10 may be a wafer, a printed circuit board and the like. In FIG. 1 the object is irradiated by a beam 90. The object 10 may be illuminated with more than a single beam.

Figure 3:
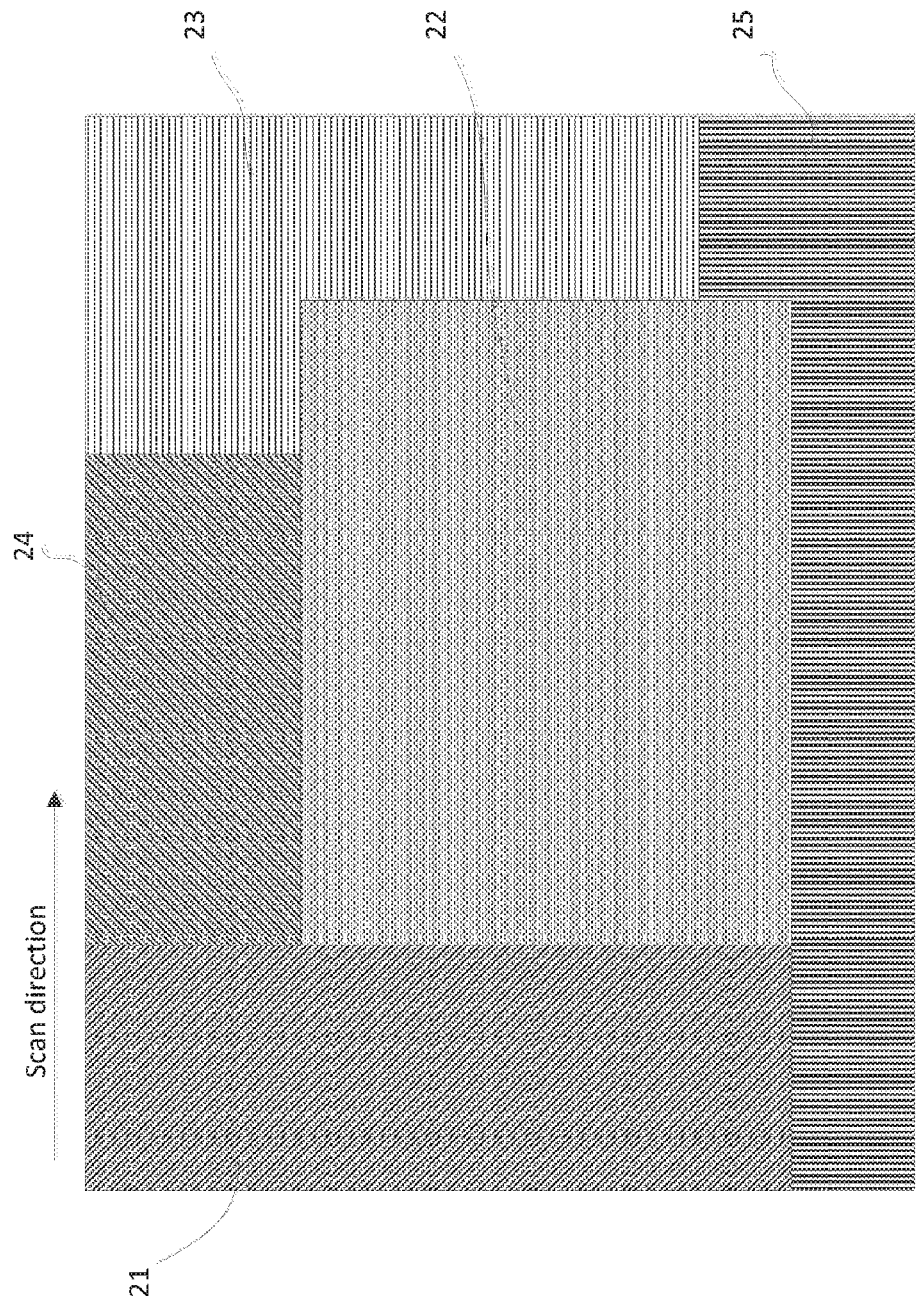
FIG. 3 illustrates an inspected object that has five areas of five different types according to an embodiment of the invention.

Object 10 may include different areas such as first area 21, second area 22, third area 23, fourth area 24 and fifth area 25 of FIG. 3. The number of different areas may differ from five areas. The shapes and sizes of the different area of the object may differ from those illustrated in FIG. 3.

The acquisition of an image of the first area is associated with a first area noise power spectrum and a first signal power spectrum.

First area 21 belongs to a first type of area and is inspected using a first configuration of the configurable image acquisition channel 70.

The acquisition of an image of the second area is associated with a second area noise power spectrum and a second signal power spectrum.

Second area 22 is of a second type of areas and is inspected using a second configuration of the configurable image acquisition channel 70.

The acquisition of an image of the third area is associated with a third area noise power spectrum and a third signal power spectrum.

Third area 23 is of a third type of areas and is inspected using a third configuration of the configurable image acquisition channel 70.

The acquisition of an image of the fourth area is associated with a fourth area noise power spectrum and a fourth signal power spectrum.

Fourth area 24 is of a fourth type of areas and is inspected using a fourth configuration of the configurable image acquisition channel 70.

The acquisition of an image of the fifth area is associated with a fifth area noise power spectrum and a fifth signal power spectrum.

Fifth area 25 is of a fifth type of areas and is inspected using a fourth configuration of the configurable image acquisition channel 70.

The first image type, the second image type, the third image type, the fourth image type and the fifth image type differ from each other. For example, the first type may include memory cells or a certain type of ordered areas of a die while the second type may include logic or unordered area of the die.

Accordingly—there is a difference between the first configuration of the configurable image acquisition channel, the second configuration of the configurable image acquisition channel, the third configuration of the configurable image acquisition channel, the fourth configuration of the configurable image acquisition channel, and the fifth configuration of the configurable image acquisition channel. For example—the poles, coefficients and/or a configurable digital filter of the configurable image acquisition channel may differ from one configuration of the configurable image acquisition channel to the other.

According to an embodiment of the invention, memory module 61 may be arranged to store (a) first noise power spectrum information about noises associated with an acquisition of an image of the first area of an inspected object, (b) first signal power spectrum information about first area signals that are associated with the acquisition of the image of the first area, (c) second noise power spectrum information about noises associated with an acquisition of an image of the second area of the inspected object, (d) second signal power spectrum information about second area signals that are associated with the acquisition of the image of the second area; (e) third noise power spectrum information about noises associated with an acquisition of an image of a third area of an inspected object, (f) third signal power spectrum information about third area signals that are associated with the acquisition of the image of the third area, (g) fourth noise power spectrum information about noises associated with an acquisition of an image of a fourth area of the inspected object, (h) fourth signal power spectrum information about fourth area signals that are associated with the acquisition of the image of the fourth area, (i) fifth noise power spectrum information about noises associated with an acquisition of an image of a fifth area of the inspected object, and (j) fifth signal power spectrum information about fifth area signals that are associated with the acquisition of the image of the fifth area.

Because the first and fourth areas are of the same type, the memory module 61 may store additional noise power spectrum information about noises associated with an acquisition of an image of the fourth area of the inspected object instead or in addition to the first noise power spectrum information. The same applies to additional signal power spectrum information.

Assuming that N is a positive integer that exceeds one. If there are N types of areas, then the memory module 61 may store N different area signal power spectrum information and N different area noise power spectrum information.

The first to fifth noise power spectrum information and/or the first to fifth signal power spectrum information can be calculated by the inspection system 50, fed to the inspection system 50, fed to the inspection system and updated by the inspection system and the like.

The first to fifth noise power spectrum information and/or the first to fifth signal power spectrum information can be calculated during a learning phase or a tuning phase in any manner.

Controller 62 may be arranged to:

Determine, in response to a first frequency wise relationship between the first noise power spectrum and the first signal power spectrum, the first configuration of the configurable acquisition channel.

Determine, in response to a second frequency wise relationship between the second noise power spectrum and the second signal power spectrum, the second configuration of the configurable acquisition channel.

Determine, in response to a third frequency wise relationship between the third noise power spectrum and the third signal power spectrum, the third configuration of the configurable acquisition channel.

Determine, in response to a fourth frequency wise relationship between the fourth noise power spectrum and the fourth signal power spectrum, the fourth configuration of the configurable acquisition channel.

Determine, in response to a fifth frequency wise relationship between the fifth noise power spectrum and the fifth signal power spectrum, the fifth configuration of the configurable acquisition channel.

Configurable image acquisition channel 70 may be arranged to:

Acquire the image of the first area 21 while being configured according to the first configuration.

Acquire the image of the second area 22 while being configured according to the second configuration.

Acquire the image of the third area 23 while being configured according to the third configuration.

Acquire the image of the fourth area 24 while being configured according to the fourth configuration.

Acquire the image of the fifth area 25 while being configured according to the fifth configuration.

Image processor 63 may be adapted to (a) process the image of the first area to generate a first area inspection result, (b) process the image of the second area to generate a second area inspection result, (c) process the image of the third area to generate a third area inspection result, (d) process the image of the fourth area to generate a fourth area inspection result, and (e) process the image of the fifth area to generate a fifth area inspection result.

The first to fifth inspection results can, for example, provide information about suspected defects that exist in the first to fifth areas respectively. The processing may apply any known comparison algorithm including die-to-die comparison, cell-to-cell comparison, die to reference comparison, and the like.

Any one of the first to fifth noise power spectrum may represent one or more noises out of (a) "thermal" noise, shot noise, and any other noise, having a constant ("white") spectrum, (b) "dark" noise of analog amplifier 72, which often rises with frequency up to the certain frequency value, (c) "flicker" noise—a low frequency noise falling with frequency, and (d) "wafer" and "system" noise, caused by non-ideality of system operation, like mechanical noise, light intensity variation in time, target wafer process variations, etc. Naturally, a spectrum of these noises are often concentrated at low frequencies.

According to an embodiment of the invention the image processor may be arranged to define, for each given area a given region that includes all the pixels of the given area as well additional pixels that surround the given area. The additional pixels belong to areas that differ from the given area and are adjacent to the given area.

The region is defined in order to compensate for loss of information resulting from performing digital filtering operations.

The selection of the additional pixels is responsive to the size of the filter and should be large enough to fill the filter regardless of the pixel of the given area that is being filtered.

For example, when using a filter that is represented by a rectangular kernel of n rows by m columns, the additional pixels may include m pixels per each row of the given area and n pixels per each column of the given area.

Figure 4:
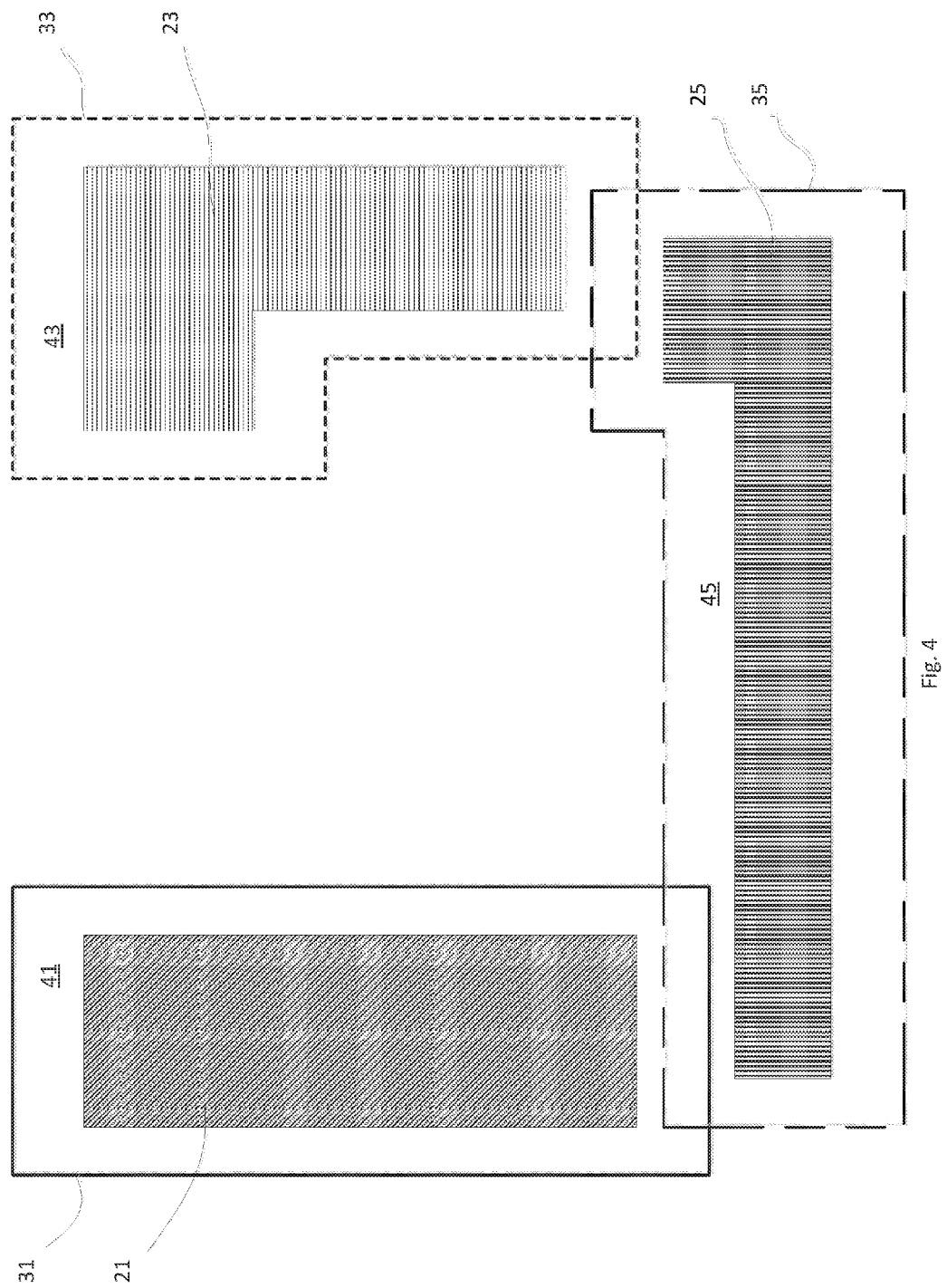
Figure 6:
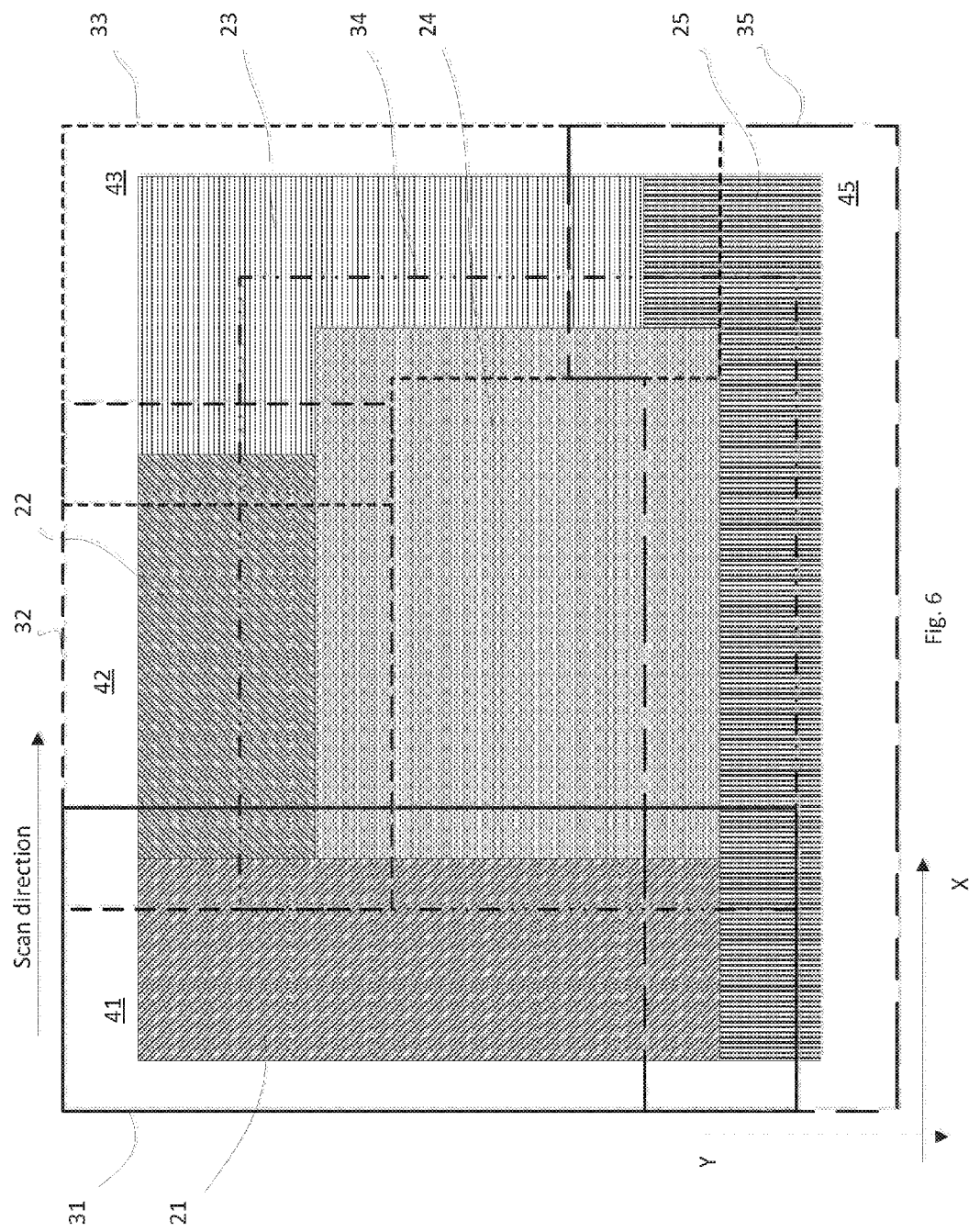

FIGS. 4, 5 and 6 illustrate (a) first region 31 having an image that is obtained by surrounding the image of first area 21 by first additional pixels 41, (b) second region 32 having an image that is that is obtained by surrounding the image of second area 22 by second additional pixels 42, (c) third region 33 having an image that is obtained by surrounding the image of third area 23 by third additional pixels 43, (d) fourth region 34 having an image that is obtained by surrounding the image of fourth area 24 by fourth additional pixels 44, and (e) fifth region 35 having an image that is obtained by surrounding the image of fifth area 25 by fifth additional pixels 45.

In many cases the areas may differ by shape and size from the shape and size of slices. The overlap area between adjacent slices can be wide enough to include enough additional pixels so that a region may be defined within a slice while using the overlap pixels.

The image processor may process images of the first to fifth regions in various manners (for example apply any comparison algorithm) to provide intermediate results. The intermediate results may include filtered images of the different regions. The filtered images are filtered using the filters that are tailored according to the type of the areas included within the regions.

Information about the additional pixels may be deleted from the intermediate results to provide information about the first to fifth areas—after being filtered.

Figure 7:
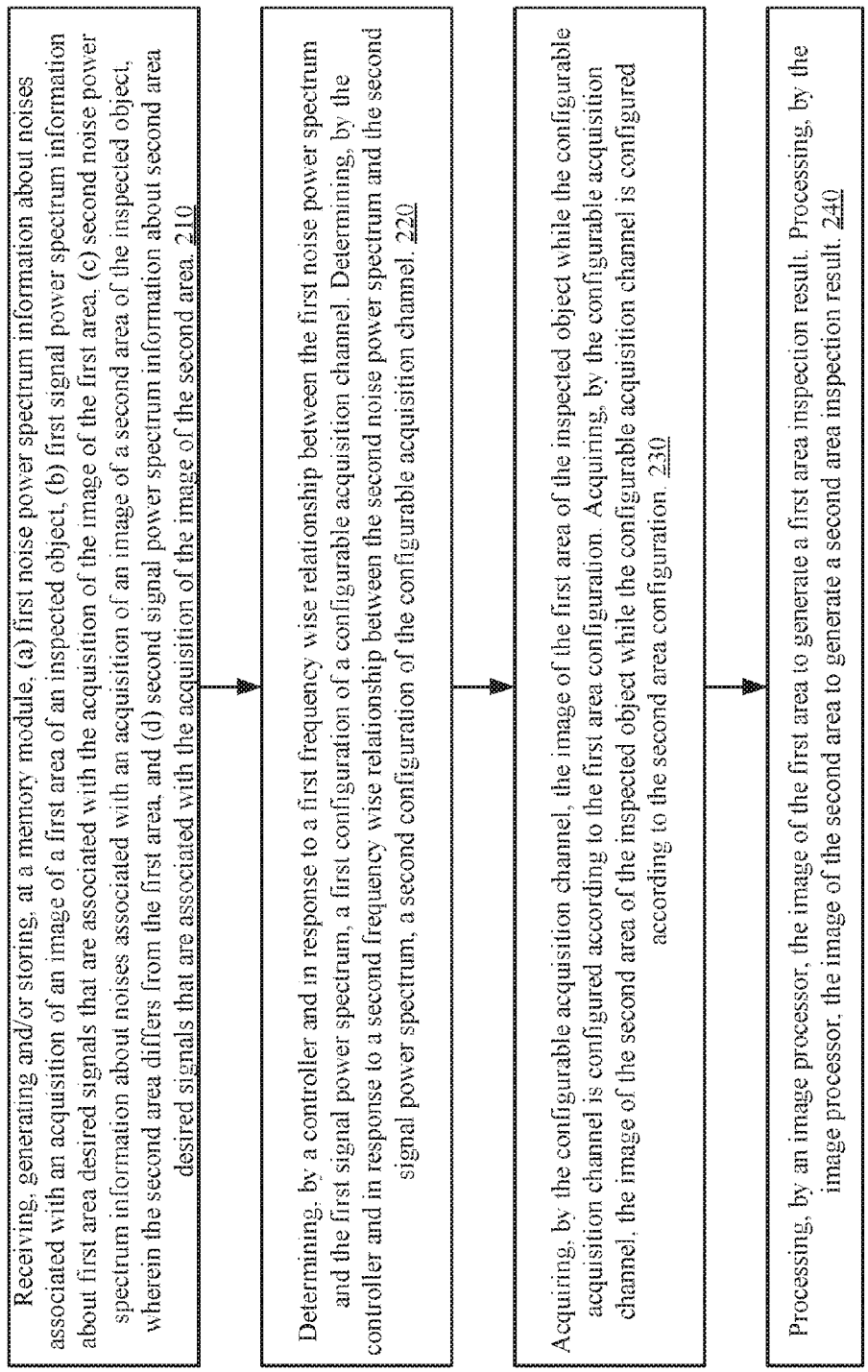
FIG. 7 illustrates a method according to an embodiment of the invention.

FIG. 7 illustrates method 200 according to an embodiment of the invention.

It is assumed that method 200 is applied on a first area and a second area that belong to different types of areas. Method 200 may be applied to any number of areas that belong to any number of types.

Method 200 may include the following sequence of steps:

Receiving, generating and/or storing (210), at a memory module, (a) first noise power spectrum information about noises associated with an acquisition of an image of a first area of an inspected object, (b) first signal power spectrum information about first area signals that are associated with the acquisition of the image of the first area, (c) second noise power spectrum information about noises associated with an acquisition of an image of a second area of the inspected object, wherein the second area differs from the first area, and (d) second signal power spectrum information about second area signals that are associated with the acquisition of the image of the second area.

Determining (220), by a controller and in response to a first frequency wise relationship between the first noise power spectrum and the first signal power spectrum, a first configuration of a configurable acquisition channel. Step 220 may also include determining, by the controller and in response to a second frequency wise relationship between the second noise power spectrum and the second signal power spectrum, a second configuration of the configurable acquisition channel. Any configuration of the configurable acquisition channel can be done during the tuning of the inspection system, during the inspection itself and/or after obtaining inspection results.

Acquiring (230), by the configurable acquisition channel, the image of the first area of the inspected object while the configurable acquisition channel is configured according to the first area configuration. Step 230 may also include acquiring, by the configurable acquisition channel, the image of the second area of the inspected object while the configurable acquisition channel is configured according to the second area configuration.

Processing (240), by an image processor, the image of the first area to generate a first area inspection result. Step 240 may also include processing, by the image processor, the image of the second area to generate a second area inspection result.

Step 240 may include at least one of the following: (a) generating a first region by surrounding the image of the first area with first additional pixels, (b) processing the first region to provide a first area inspection result, (c) generating a second region by surrounding the image of the second area with second additional pixels, (d) processing the second region to provide a second area inspection result.

According to an embodiment of the invention images of the different regions may be processed in parallel. When there are additional pixels that are associated with more than a single region, these additional pixels are cloned and provided to both processes.

According to an embodiment of the invention the image processing is executed one slice after the other. The pixels of the slice may be processed by one digital filter after the other or may be processed in parallel by different filters. When the pixels of a slice are processed in parallel there may be a need to clone the entire slice or parts of the slice.

Figure 8:
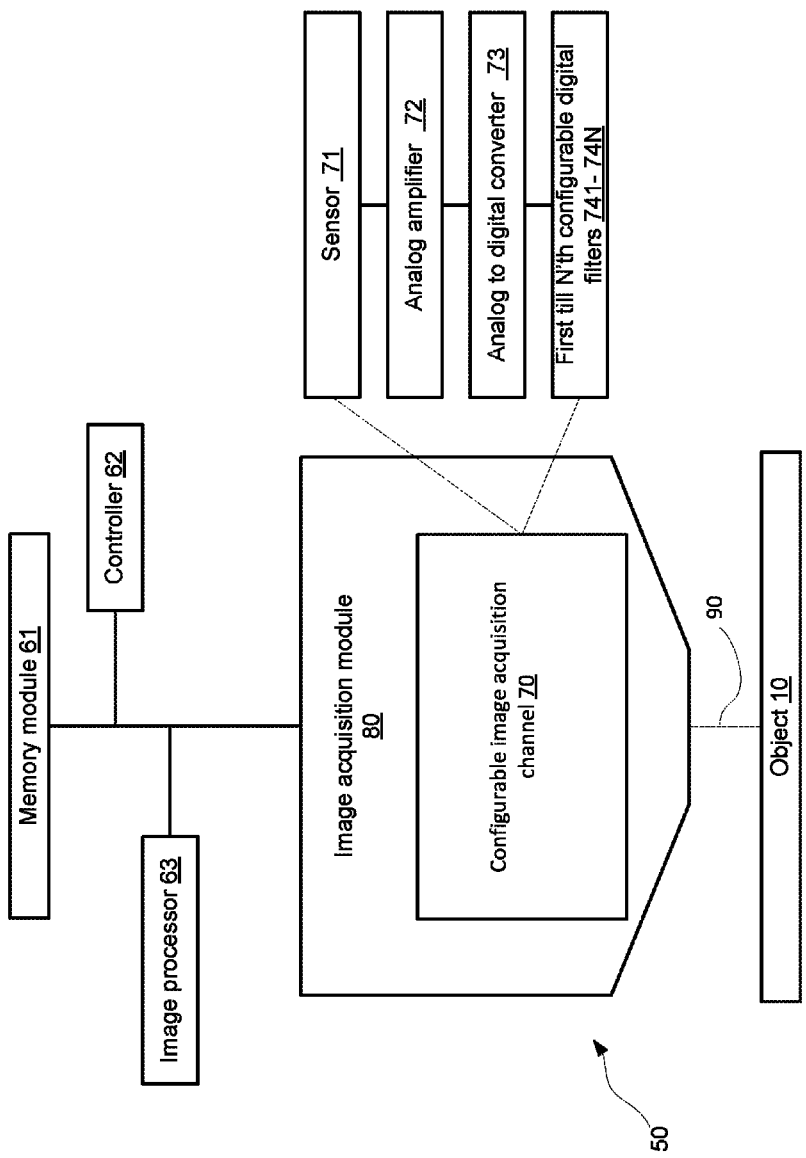
FIG. 8 illustrates a system according to an embodiment of the invention.

FIG. 8 illustrates a system that includes N different configurable filters (N being a positive integer that exceeds 1) denoted 741-74N. Assuming that N equals five than there are five configurable digital filters and the acquired slices may be filtered in parallel by a five configurable digital filters that are configured according to the first to fifth configurations of the configurable image acquisition respectively.

When the entire slice is cloned and provided to different configurable digital filters, the image processing may include selecting which filtered pixels to ignore and which filtered pixels should be used to form a filtered image of the slice.

FIG. 9 illustrates two slices 17 and 18 and multiple regions according to an embodiment of the invention.

Slice 17 includes a first group 411 of first additional pixels, a first group 211 of first area pixels, a first group 251 of fifth area pixels 25, and a first group 451 of fifth additional pixels.

When slice 17 is fed to first to fifth configurable digital filters, the output of second, third and fourth configurable digital filters can be ignored as slice 17 covers pixels that belong to the first and fifth regions only. The filtered pixels outputted from the first configurable digital filter that correspond to first group 211 of first area pixels may be taken into account. The filtered pixels outputted from the fifth configurable digital filter that correspond to first group 251 of fifth area pixels may be taken into account.

Slice 18 includes a first group 431 of third additional pixels, a first group 231 of third area pixels, a second group 252 of fifth area pixels, and a second group 452 of fifth additional pixels.

When slice 18 is fed to first to fifth configurable digital filters, the output of first, second, and fourth configurable digital filters can be ignored—as slice 18 covers pixels that belong to the third and fifth regions only. The filtered pixels outputted from the third configurable digital filter that correspond to first group 231 of third area pixels may be taken into account. The filtered pixels outputted from the fifth configurable digital filter that correspond to second group 252 of fifth area pixels may be taken into account.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of step in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described steps are merely illustrative. The multiple may be combined into a single step, a single step may be distributed in additional steps and steps may be executed at least partially overlapping in time. Moreover, alternative embodiments may include multiple instances of a particular step, and the order of steps may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

I claim:

1. An inspection system, comprising:
a memory module that is adapted to store: (a) first noise power spectrum information about noises associated with an acquisition of an image of a first area of an inspected object, (b) first signal power spectrum information about first area signals that are associated with the acquisition of the image of the first area, (c) second noise power spectrum information about noises associated with an acquisition of an image of a second area of the inspected object, wherein the second area differs from the first area, and (d) second signal power spectrum information about second area signals that are associated with the acquisition of the image of the second area;
a configurable acquisition channel;
a controller that is adapted to: (a) determine, in response to a first frequency wise relationship between the first noise power spectrum and the first signal power spectrum, a first configuration of the configurable acquisition channel; and (b) determine, in response to a second frequency wise relationship between the second noise power spectrum and the second signal power spectrum, a second configuration of the configurable acquisition channel; and
wherein the configurable acquisition channel is adapted to: (a) acquire the image of the first area of the inspected object while being configured according to the first configuration, and (b) acquire the image of the second area while being configured according to the second configuration.

2. The inspection system according to claim 1, further comprising an image processor that is adapted to (a) process the image of the first area to generate a first area inspection result and to (b) process the image of the second area to generate a second area inspection result.

3. The inspection system according to claim 1, further comprising an image processor that is adapted to: (a) generate an image of a first region by surrounding the image of the first area with first additional pixels; (b) process the image of the first region to provide a first area inspection result; (c) generate an image of a second region by surrounding the image of the second area with second additional pixels; and (d) process the image of the second region to provide a second area inspection result.

4. The inspection system according to claim 1 wherein the first frequency wise relationship is a frequency wise ratio between the first signal power spectrum and the first noise power spectrum; and wherein the second frequency wise relationship is a frequency wise ratio between the second signal power spectrum and the second noise power spectrum.

5. The inspection system according to claim 1 wherein the first frequency wise relationship is a frequency wise ratio between the first signal power spectrum and a square of the first noise power spectrum; and wherein the second frequency wise relationship is a frequency wise ratio between the second signal power spectrum and a square of the second noise power spectrum.

6. The inspection system according to claim 1 wherein the first area and the second area are selected so that the first frequency wise relationship differs from the second frequency wise relationship.

7. A method for inspecting an inspected object, the method comprising:
storing, at a memory module, (a) first noise power spectrum information about noises associated with an acquisition of an image of a first area of an inspected object, (b) first signal power spectrum information about first area signals that are associated with the acquisition of the image of the first area, (c) second noise power spectrum information about noises associated with an acquisition of an image of a second area of the inspected object, wherein the second area differs from the first area, and (d) second signal power spectrum information about second area signals that are associated with the acquisition of the image of the second area;
determining, by a controller and in response to a first frequency wise relationship between the first noise power spectrum and the first signal power spectrum, a first configuration of a configurable acquisition channel;
determining, by the controller and in response to a second frequency wise relationship between the second noise power spectrum and the second signal power spectrum, a second configuration of the configurable acquisition channel;
acquiring, by the configurable acquisition channel, the image of the first area of the inspected object while the configurable acquisition channel is configured according to the first configuration; and
acquiring, by the configurable acquisition channel, the image of the second area of the inspected object while the configurable acquisition channel is configured according to the second configuration.

8. The method according to claim 7, further comprising processing, by an image processor, the image of the first area to generate a first area inspection result; and processing, by the image processor, the image of the second area to generate a second area inspection result.

9. The method according to claim 7, wherein the configurable acquisition channel comprises a configurable digital filter that has a first area filter configuration and a second area filter configuration; and wherein a number of first additional pixels is responsive to a size of the configurable digital filter.

10. The method according to claim 7, wherein the first frequency wise relationship is a frequency wise ratio between the first signal power spectrum and the first noise power spectrum; and wherein the second frequency wise relationship is a frequency wise ratio between the second signal power spectrum and the second noise power spectrum.

11. The method according to claim 7, wherein the first frequency wise relationship is a frequency wise ratio between the first signal power spectrum and a square of the first noise power spectrum; and wherein the second frequency wise relationship is a frequency wise ratio between the second signal power spectrum and a square of the second noise power spectrum.

12. The method according to claim 7, wherein the first area and the second area are selected so that the first frequency wise relationship differs from the second frequency wise relationship.

13. A non-transitory computer readable medium that stores instructions that once executed by a computer cause the computer to perform steps comprising:

storing (a) first noise power spectrum information about noises associated with an acquisition of an image of a first area of an inspected object, (b) first signal power spectrum information about first area signals that are associated with the acquisition of the image of the first area, (c) second noise power spectrum information about noises associated with an acquisition of an image of a second area of the inspected object, wherein the second area differs from the first area, and (d) second signal power spectrum information about second area signals that are associated with the acquisition of the image of the second area;

determining, in response to a first frequency wise relationship between the first noise power spectrum and the first signal power spectrum, a first configuration of a configurable acquisition channel;

determining, in response to a second frequency wise relationship between the second noise power spectrum and the second signal power spectrum, a second configuration of the configurable acquisition channel;

acquiring the image of the first area of the inspected object while the configurable acquisition channel is configured according to the first configuration; and acquiring the image of the second area of the inspected object while the configurable acquisition channel is configured according to the second configuration.

14. The non-transitory computer readable medium according to claim 13, further comprising instructions for processing, by an image processor, the image of the first area to generate a first area inspection result; and instructions for processing, by the image processor, the image of the second area to generate a second area inspection result.

15. The non-transitory computer readable medium according to claim 13, wherein the configurable acquisition channel comprises a configurable digital filter that has a first area filter configuration and a second area filter configuration; and wherein a number of first additional pixels is responsive to a size of the configurable digital filter.

* * * * *